United States Patent [19]

Hatakeyama

[11] Patent Number: 4,725,232
[45] Date of Patent: Feb. 16, 1988

[54] DENTAL THERAPEUTICAL APPARATUS

[75] Inventor: Narito Hatakeyama, Funabashi, Japan

[73] Assignee: Kabushiki Kaisha Yoshida Seisakusho, Tokyo, Japan

[21] Appl. No.: 761,632

[22] Filed: Aug. 1, 1985

[51] Int. Cl.⁴ .............................................. A61C 1/02
[52] U.S. Cl. ..................................... 433/98; 433/126
[58] Field of Search ..................... 433/98, 126, 88, 99, 433/103, 131

[56] References Cited

U.S. PATENT DOCUMENTS

| | | | |
|---|---|---|---|
| 3,213,537 | 10/1956 | Balamuth et al. | 433/98 |
| 3,556,669 | 1/1977 | Valeska et al. | 433/98 |
| 3,886,660 | 6/1975 | Thornton, Jr. et al. | 433/98 |
| 3,959,882 | 6/1976 | Rackson | 433/98 |
| 4,080,737 | 3/1978 | Fleer | 433/126 |
| 4,136,450 | 1/1979 | Guenther et al. | 433/98 |
| 4,249,901 | 2/1981 | Wieser | 433/98 |
| 4,494,932 | 1/1985 | Rzewinski | 433/88 |
| 4,514,172 | 4/1985 | Behringer | 433/126 |

*Primary Examiner*—John J. Wilson
*Attorney, Agent, or Firm*—Jordan and Hamburg

[57] ABSTRACT

A dental therapeutical apparatus comprising a plurality of utility units selectively connectable to a common energy supply unit, each of the utility units having different uses and being furnished with a form of energy suited for the therapeutical units.

9 Claims, 4 Drawing Figures

DENTAL THERAPEUTICAL APPARATUS

FIELD OF THE INVENTION

The present invention relates to a dental therapeutical apparatus, and more specifically to a dental therapeutical apparatus having a plurality of utility units selectively connectable to a common energy supply unit, each of the utility units being designed so that exclusive therapeutical units having different uses are applied in the form of an energy suited to the therapeutical units.

BACKGROUND OF THE INVENTION

In a dental therapeutical field, a variety of tools are required. Most of these therapeutical instruments are applied with energies in some different forms such as air, water, electric power, light and the like. A handpiece for cutting teeth requires compression air for rotating a grinder at a high speed and high pressure water used for cleaning. An ultrasonic therapeutical instrument having a cutter blade or a scaler requires a high frequency power source for driving an acoustical transducer for producing high frequency vibrations at an operating end thereof, and a photo-radiator for producing a photo-polymerization of a dental resin requires a visual beam. Recently, a polishing powder jet flow for polishing the surface of teeth and a laser beam source for a coagulator are also required. Generally, there are many forms and kinds of final energies required but ultimate energies sources are high pressure air and high pressure water. Electricity is considered to belong to an intermediate energy form since it can be generated by other energy source, i.e., high pressure air or high pressure water. Even therapeutical instruments of the different types which consume the same kind of energy, the rating of energy thereof is usually different. Thus, in order to individually actuate many therapeutical instruments, energies in the form suited to these instruments, respectively, have to be supplied, as a consequence of which a dental therapeutical room is unavidably equipped with many energy supply units of the same kind. In this case, if different types of therapeutical instruments having the same energy supply unit are to be provided, this can be attained by providing each therapeutical instrument with an adapter which converts an energy received from the aforesaid supply unit into one suited to the therapeutical instrument. However, such a measure poses a disadvantage that individual therapeutical instruments become large-sized, which is not tolerable for a dentist. In many dental therapeutical rooms, there are provided some supplies comprising a combination of high pressure air and high pressure water, and a dentist connects a desired therapeutical instrument to a selected one of supply ports. Usually, a supply port is installed on a dental chair or an operating arm extended therefrom. Three to five ports are provided, and a therapeutical instrument having a different type or rating is selectively connected to each of such supply ports. The supply port in combination of high pressure air and high pressure water is made in the form of a quick engagement or a releasable connector, on which a power channel is also provided. Various types of connectors applicable to such supply ports are known, typical examples of which are disclosed in the following:

Japanese Patent Publication No. 45-30434
Japanese Utility Model Publication No. 39-24590
Japanese Utility Model Publication No. 50-11347
Japanese Utility Model Publication No. 50-11348
Japanese Utility Model Publication No. 50-15903
Japanese Utility Model Publication No. 50-15196
Japanese Utility Model Publication No. 54-27279
Japanese Patent Laid-Open No. 58-4546
Japanese Patent Laid-Open No. 58-5588

SUMMARY OF THE INVENTION

It is an object of the present invention to provide a dental therapeutical apparatus including a plurality of utility units which enable use of different types of many therapeutical instrument units by minimum energy supply units.

It is a further object of the invention to provide a dental therapeutical apparatus which can make a therapeutical instrument unit small in size and lightweight which is held by a hand of a dentist.

In accordance with the present invention, there is provided a dental therapeutical apparatus comprising a common energy supply unit for supplying a plurality of energies of different forms, a plurality of utility units selectively connectable to the energy supply unit, connection means for selectively connecting the energy supply unit and each of the utility units, which supplies the energy in the form selected out of the plurality of energies to each of the utility units, and a therapeutical instrument unit adapted for therapeutical purposes different from each other, the therapeutical unit being connected to each of the utility units, each of the utility units having a transducer for converting at least one of input energies in the selected form into an output energy adapted for the terapeutical instrument unit corresponding to the utility unit, the therapeutical instrument unit being acutated by the output of the transducer means.

According to a preferred embodiment of the present invention, the common energy supply unit is able to supply high pressure air, high pressure water and electric power, and each utility unit receives at least one selected form of energy out of the energies to convert the thus selected form of input energy into a different form of output energy or convert into the same form but different rating of output energy. The group of the therapeutical units seek a variety of forms or ratings of energies, and each utility unit executes a variety patterns of converting operations to response to the aforesaid requirements. In a typical utility unit, the utility unit receives compression high pressure air as an input energy to thereby drive a small type turbine generator to release its electric energy. This output electric energy can be of the type which actuates an acoustic transducer of an ultrasonic therapeutical instrument unit. As the case may be, the aforesaid electric energy is formed into an intemediate energy by which a halogen lamp is lighted and an output light energy may be fed to a photo-radiator as a therapeutical instrument unit. Alternatively, according to an example of a separate utility unit, the unit receives high pressure air as well as high pressure water as an input energy, the high pressure air energy being converted into an electric energy through the small type turbine generator, and this electric energy is fed to a heater for heating the high pressure water. As the result, the high pressure hot water is supplied as an output energy from the utility unit to a hot water cleaner.

DESCRIPTION OF THE PREFERRED EMBODIMENTS

Figure 1:
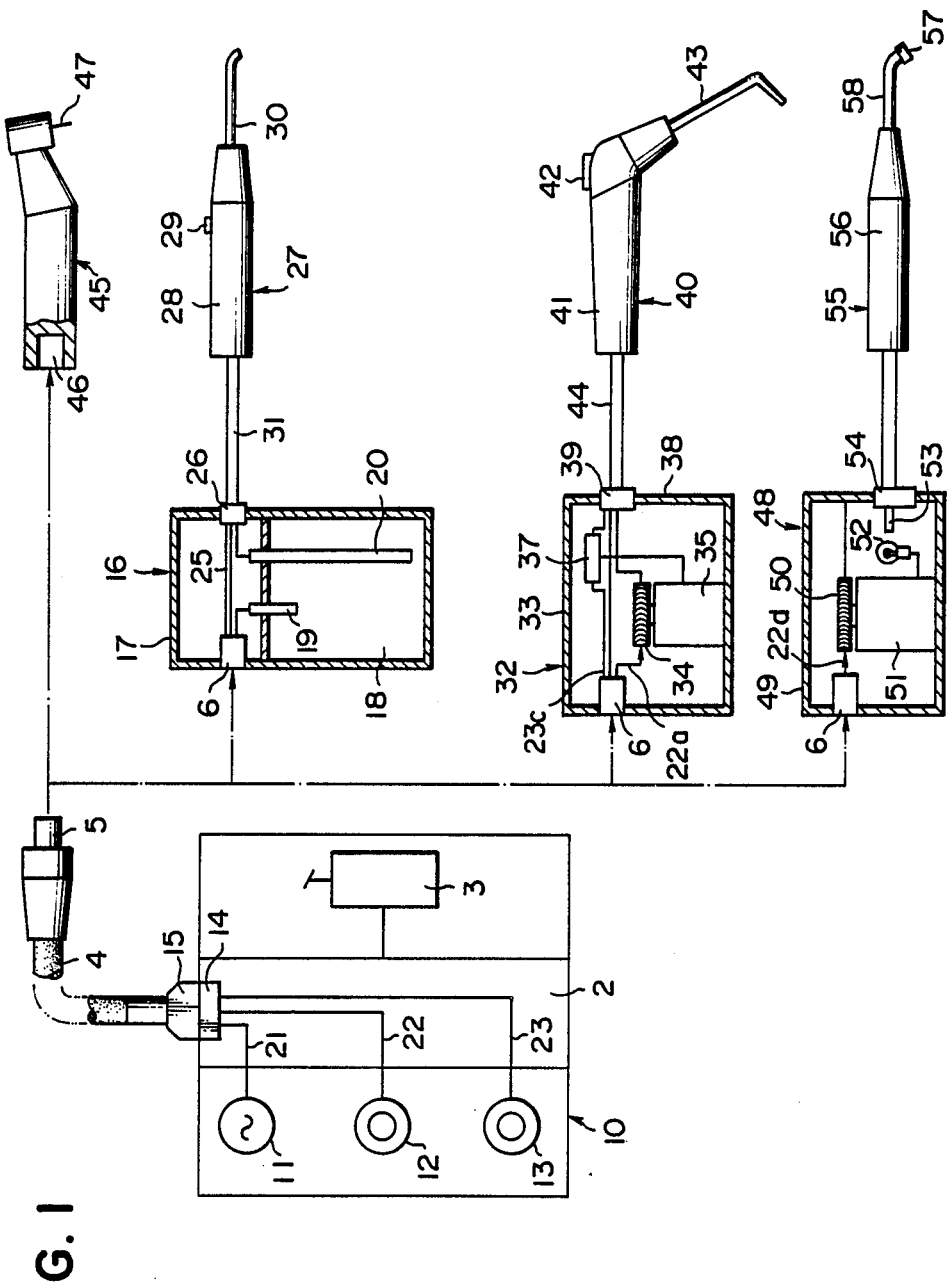
FIG. 1 is an explanatory view pictorially showing a dental therapeutical apparatus according to the present invention comprising a plurality of utility units selectively connectable to a common energy supply unit and a therapeutical instrument unit.

Referring to FIG. 1, the dental therapeutical apparatus according to the present invention comprises a common energy supply unit 10 which includes a power source 11, a high pressure air source 12 and a high pressure water source 13. Each of these sources is controlled ON and OFF by a controller 2 including a foot switch 3. This controller 2 is provided with a socket 14 in communication with supply passages 21, 22 and 23 extended from the energy sources 11, 12 and 13, said socket 14 having a plug 15 connected thereto, the plug 15 being provided on the other end of a composite supply channel member 4 having at one end a coupling member 5. The composite supply channel member 4 is a handle for three energy supply channels including an insulated electric conductor, a high pressure air hose and a high pressure water hose.

A few utility units 16, 32 and 48 selectively connectable to the common energy supply unit 10 are shown but the utility units are provided with exclusive therapeutical instrument units 27, 40 and 55, respectively. In the illustrated embodiment, the first utility unit 16 is used to supply a high pressure medicinal liquid to the therapeutical instrument unit 27 which functions as a syringe. The first utility unit 16 is provided with a housing 17 including a medicinal liquid tank 18, the housing 17 having an inlet coupling 6 and an outlet socket 26. Positioned internally of the medicinal liquid tank 18 are an opening end of a jet pipe 19 extending from the inlet coupling 6 and an inlet opening of a discharge pipe 20 in communication with the outlet socket 26. A tube or hose member 31 having a suitable length extending from the syringe 27 is fixedly or detachably connected to the outlet socket 26. The syringe 27 comprises a handle 28 and a nozzle member 30 mounted on the handle, include a valve operating button 29 around the handle 38. The valve operating button 29 is used to open and close a valve (not shown) provided between the hose member 31 and the nozzle 30. The inlet coupling 6 is matched so as to receive the outlet coupling 5 of the composite supply channel member 4 connected to the common energy supply unit 10. The outlet coupling 5 and the inlet coupling 6 may be of a well known dental coupling of the quick engaging or quick releasing type, which may be similar to that disclosed for example in Japanese Utility Model Publication No. 58-22728. The inlet coupling 6 of the first utility unit 16 is in the state that electric power, high pressure air and high pressure water may be received from the common energy supply unit 10 through three channels. In this case, however, the channels for electric power and high pressure water are made blind and only the channel for high pressure air is connected to a jet pipe 19. In use, a predetermined medicinal liquid is charged into the tank 18 and thereafter the operating switch 3 of the energy supply unit 10 is turned ON, then the high pressure air is introduced into the medicinal liquid tank 18 through the jet pipe 19 and the tank acts as a mixer so that the high pressure air including scattered medicinal liquid or the high pressurized medicinal liquid is supplied to the syringe 27 through a discharge pipe 20. If a polishing powder such as NaHCO in place of the medicinal liquid is put into the tank 18, the syringe 27 can be used for polishing the surface of teeth.

Th second utility unit 32 is used for a supply of high pressure hot water in cooperation with a water cleaning head as a therapeutical instrument unit 40. The water cleaning head 40 is often used to clean the teeth and oral cavity, and the handle 41 thereof has at an end an injection nozzle member 43 and at a shoulder a valve operating button 42. The second utility unit 32 is provided with a housing 33 having an inlet coupling 6 and an outlet socket 39. The inlet coupling 6 receives an outlet coupling 5 of the composite supply channel member 4 extending from the energy supply unit 10 similar to the previously mentioned embodiment to draw the energy channels into the housing 33. The housing 33 is internally provided with a dynamo generator 35 including an impellar 34 similar to that generally provided within the handpiece and a heater 37 for an electric water heater. The impeller 34 is installed within the high pressure air channel 22C from the inlet coupling 6 toward the outlet socket 39 in a known manner, whereas the heater 37 for an electric water heater is provided so as to surround the high pressure water channel 23C from the inlet coupling 6 toward the outlet socket 39. This heater 37 is supplied with an outlet electric energy generated by the dynamo-generator 35 by rotation of the impeller 34. The second utility unit 32 and the water cleaning head 40 are brought into communication with each other by a hose member 44 for connecting the second channel fixedly or detachably connected to the outlet socket 39 so that high pressure hot water heated by the heater 37 passing through the hose 44 and the high pressure air having passed through the impeller 34 are supplied to the head 40, in which case, the operating button 42 on the handle 41 functions to selectively or simultaneously open and close both the channels. It will be noted that a change in design can be made so that an electric heater is also provided in the high pressure air channel and high pressure air heated thereby is used to feed hot air and dry the oral cavity.

The third utility unit 48 is used in combination with a therapeutical instrument unit 5 comprising a photoradiator. This third utility unit 48 is provided with a housing 49 including an inlet coupling 6 similar to the aforementioned embodiments. The inlet coupling 6 has an outlet coupling 5 of the composite supply channel member 4 extending from the energy supply unit 10 engaged therewith, and the energy of the third channel is introduced into the housing 49 through the coupling 6. In this embodiment, however, only a high pressure air channel 22d is used and other energy channels are blocked within the inlet coupling 6 The high pressure air channel 22d within the housing 49 is opened at the end but is provided in the midst thereof an impeller 50 in a well known manner, and a dynamo-generator 51 driven by the impeller 59 is provided. An output electric energy of the dynamo-generator 51 is supplied to an electrid lamp 52 within the housing 49 to light said lamp. To one side of the housing 49 is fixed one end of an optical fiber cable 53 extending from a photo-radiator 55 by means of a support piece 54, said optical fiber cable having one end formed to be an incident opening which is opposed to the lamp 52. The photo-radiator 55 includes a handle 56 having an elongated extension 58 bearing a lens 57 at the end thereof to hold the optical fiber cable 53 reaching the lens 57 passing therethrough. Such a photo-radiator 55 can be used to illuminate the oral cavity as a pencil type lamp or can serve as a illuminating source for photo-polymerization of dental resin depending on the type of lamp used.

Preferably, in the apparatus of the present invention, the utility units 16, 32 and 48 can be used with an exchange-ability with a handpiece 45 having a known grinder 47, and thus, the inlet coupling 21 of the utility units may be matched in dimension with the inlet coupling 46 of the known handpiece 45.

Figure 2:
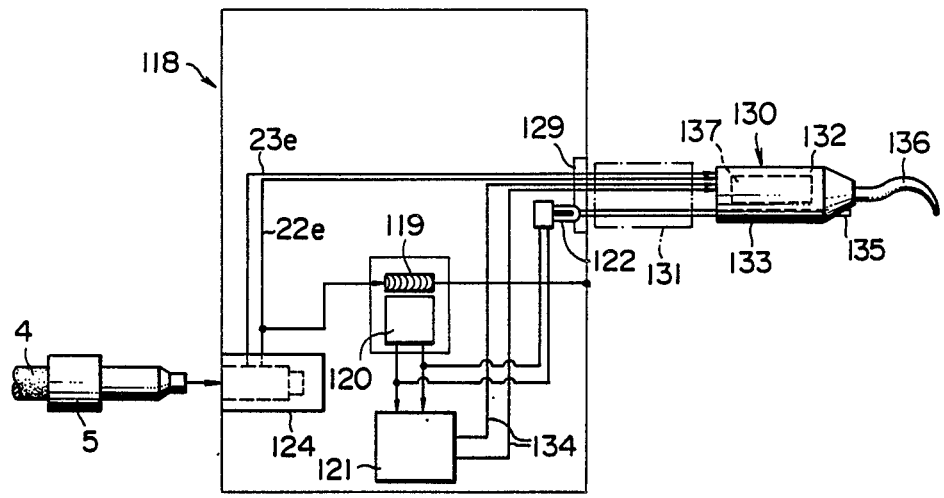
FIG. 2 is an explanatory view pictorially showing an example of another utility unit that may be used in place of one of the utility units shown in FIG. 1.

The embodiment shown in FIG. 2 is substantially the same as the utility units shown in FIG. 1 but a fourth utility unit 118 and a therapeutical instrument unit 130 which are somewhat different in design from those shown in FIG. 1 are pictorially shown. The fourth utility unit 118 is provided with a housing 118 including an inlet coupling 124 similar to that of the aforementioned embodiment. A high pressure air channel 22e and a high pressure water chanel 23e are introduced into the housing 118 through the inlet coupling 124, said channels extending toward the outlet socket 129. The high pressure air channel 22e is branched and the branched high pressure air channel is opened at the end but a dynamo-generator 120 including an impeller 119 is operatively inserted in a passage in the midst thereof. Output of the dynamo-generator 120 is fed to a power supply regulator 121 such as an electric oscillation generator, and output of the regulator 121 reaches the outlet socket 129 through an electric wire 134. The power supply regulator 121 can be of a high frequency oscillator, a supersonic oscillator or a pulse oscillator which uses output of the dynamo-generator 121 as a power source. Output of the dynamo-generator 120 serves to light a lamp 122 but the lamp 122 is positioned at the photo-channel outlet within the outlet socket 129. The therapeutical instrument unit 130 having a handle 132 is connected to an outlet socket 129 of the utility unit 118 by a connecting composite channel member 131 comprising a high pressure air channel, a high pressure water channel, a power channel and an optical channel. In this case, the optical channel includes an optical fiber cable 133, one open end of which is opposed to the lamp 122 within the outlet socket 129 whilst the other open and passes through the therapeutical instrument unit 130 and extending to a forward end 135. On a forward end 135 of the therapeutical instrument unit 130 is mounted a terminal member 136 which can be selected among the following depending on functions imposed on the therapeutical instrument unit 130. That is, it includes a therapeutical knife, a measuring stylus, a scaler, a vibrating cutting blade, a laser applicator and the like. To activate these terminal members 136, an urging means 137 is provided within the handle 132, and the urging means 137 is connected to a power source regulator 121 through a power channel within the connecting composite channel member. The power source regulator 121, the urging means 137 and the terminal member 136 are related with one another, and if one of these is selected in form, other forms are determined derivatively. They cooperate with one another to achieve the role of the therapeutical instrument. The following table shows an example of the relation between such elements as described.

| Therapeutical instrument | Form of terminal member | Type of urging means | Kind of power source regulator |
|---|---|---|---|
| Laser coagulator or knife | Probe | Semiconductor laser | Laser source |
| High frequency knife | Knife | Electric machine transducer | High frequency oscillator |
| Scaler | Bend needle | Acoustical transducer | Supersonic oscillator |

The therapeutical instrument unit 130 draws the high pressure air channel and high pressure water channel into the handle 132 thereof, and the open ends of these energy channels are open to a suitable position of the forward end 135 of the handle 132 similar to the known dental therapeutical instruments. The handle 132 may be provided with operating buttons (not shown) for opening and closing the high pressure air channel and high pressure water channel and an operating button (not shown) for the urging means 137, these buttons may be easily installed in a well known manner. It is usually desirable that one exclusive therapeutical unit 130 is combined with one utility unit 118 but as the case may be, a few power source regulators 121 of different kinds may be installed within the single utility unit 118 so that outputs thereof are selectively supplied to the outlet socket 129, and a few therapeutical instrument units of different types are selectively combined with the outlet socket 129.

Figure 3:
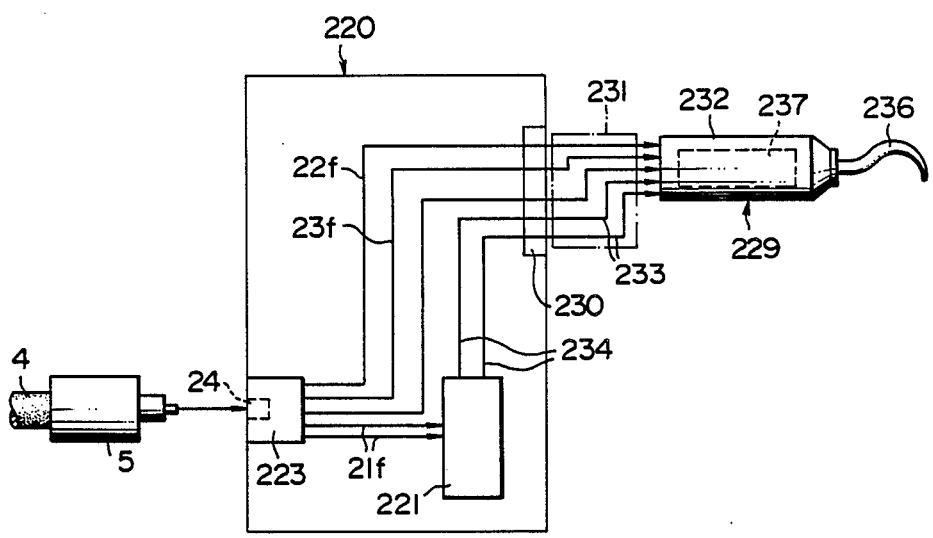
FIG. 3 is an explanatory view pictorially showing an example of a still another utility unit similar to FIG. 2.

In the embodiment shown in FIG. 3, there is provided a utility unit 220 having a power channel 21f as well as a high pressure air channel 22f and a high pressure water channel 23f. The channels are supplied with the relevant energy from an inlet coupling 223, and the high pressure air channel 22f and the high pressure water channel 23f respectively extend from the inlet coupling 233 to an outlet socket 230. The power channel 21f supplies power to a power source regulator 221, which converts a received power into an electric output suited to a predetermined rating, and the thus obtained output is supplied to the outlet socket 230 through the electric output channel 234. A therapeutical unit 229 is provided with a housing 232 similar to that shown in FIG. 2, the housing having a tool 236 provided at the distal end thereof. This unit 229 is connected to the energy channels through a connecting composite supply channel 231 extending from the outlet socket 230 of the utility unit 220. The tool 236 is activated by an urging means 237 provided internally of the housing 232, and the urging means 237 is supplied with a power from the power source regulator 221. The tool 236, urging means 237 and power source regulator 221 are related to one another similar to that described in connection with the previous embodiment.

Figure 4:
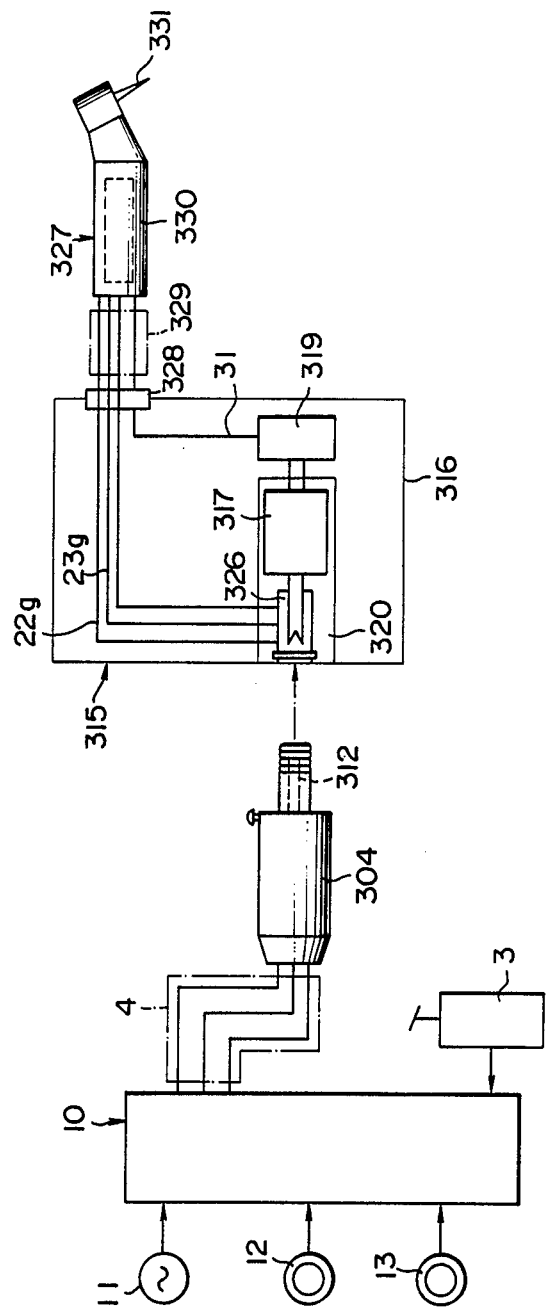
FIG. 4 is an explanatory view pictorially showing an example of another utility unit similar to FIG. 3.

Referring to FIG. 4, there is pictorially shown a utility unit 315 suitable for use with an energy supply unit 10 having, as an outlet coupling 304, a coupling with an electric micro-motor housed therein. The above-described coupling with an electric micro-motor housed therein is well known as well as a handpiece detachably engaged therewith, one example of which is disclosed in Japanese Patent Publication No. 52-43037. In the outer coupling 304 of this kind, power of the micor-motor appears in an output shaft 312 and is transmitted into the utility unit 315 through an inlet coupling 320 having a transmission shaft 326 engaging the output shaft. The utility unit 315 is provided with a dynamo-generator 317 driven by said transmission shaft 326, and output of the generator is supplied to a power source regulator 319 similar to that shown in FIG. 2. In the utility unit 315, a high pressure air channel 22g and a high pressure water channel 23g are introduced through an inlet coupling 320, and these channels are connected to an outlet socket 328. Output of the power source regulator 319 is connected to the outlet socket 328. A therapeutical unit 327 is made in a manner almost similar to the previous embodiment and receives energies from the outlet socket 328 through a connecting composite supply channel member 329. This unit 327 is internally provided with an urging means 330 driven by the power source regulator 319, the urging means 330 activating a tool 331.

What is claimed is:

1. A dental therapeutical apparatus comprising a common energy supply unit for supplying a plurality of energies of different forms, a plurality of utility units selectively connectable to the energy supply unit, connecting means for selectively connecting the energy supply unit and each of the utility units, which supplies the energy in the form selected out of the plurality of energies to each of the utility units, and a therapeutical instrument unit adapted for therapeutical purposes different from each other, the therapeutical unit being connected to each of the utility units, each of the utility units having transducing means for converting at least one of input energies in the selected form into an output energy adapted for the therapeutical instrument unit corresponding to the utility unit, the therapeutical instrument unit being actuated by the output of the transducing means, in which at least one of said transducing means in said utility units comprises a dynamo-generator which is driven by a pressurized air input energy to generate electric energy, and regulating means for electrically regulating the electric output energy of said dynamo-generator.

2. A dental therapeutical apparatus according to claim 1, wherein said regulating means comprises a high frequency oscillator.

3. A dental therapeutical apparatus according to claim 1, wherein said regulating means comprises a supersonic oscillator.

4. A dental therapeutical apparatus according to claim 1, wherein said regulating means comprises a pulse oscillator.

5. A dental therapeutical apparatus according to claim 1, wherein said regulating means comprises a laser source.

6. A dental therapeutical apparatus comprising a common energy supply unit for supplying a plurality of energies of different forms, a plurality of utility units selectively connectable to the energy supply unit, connecting means for selectively connecting the energy supply unit and each of the utility units, which supplies the energy in the form selected out of the plurality of energies to each of the utility units, and a therapeutical instrument unit adapted for therapeutical purposes different from each other, the therapeutical unit being connected to each of the utility units, each of the utility units having transducing means for converting at least one of input energies in the selected form into an output energy adapted for the therapeutical instrument unit corresponding to the utility unit, the therapeutical instrument unit being actuated by the output of the transducing means, in which at least one of said transducing means in said utility units comprises a dynamo-generator which is driven by a pressurized air input energy to generate electric energy, and an electric lamp which is energized by the electric output of said dynamo-generator.

7. A dental therapeutical apparatus comprising a common energy supply unit for supplying a plurality of energies of different forms, a plurality of utility units selectively connectable to the energy supply unit, connecting means for selectively connecting the energy supply unit and each of the utility units, which supplies the energy in the form selected out of the plurality of energies to each of the utility units and a therapeutical instrument unit adapted for therapeutical purposes different from each other, the therapeutical unit being connected to each of the utility units, each of the utility units having transducing means for converting at least one of input energies in the selected form into an output energy adapted for the therapeutical instrument unit corresponding to the utility unit, the therapeutical instrument unit being actuated by the output of the transducing means, in which at least one of said transducing means in said utility units comprises a dynamo-generator which is driven by a pressurized air input energy to generate electric energy, and an electric heater which is energized by the electric output of said dynamo-generator for heating one of an input pressurized water and an input pressurized air.

8. A dental therapeutical apparatus comprising a common energy supply unit for supplying a plurality of energies of different forms, a plurality of utility units selectively connectable to the energy supply unit, connecting means for selectively connecting the energy supply unit and each of the utility units, which supplies the energy in the form selected out of the plurality of energies to each of the utility units, and a therapeutical instrument unit adapted for therapeutical purposes different from each other, the therapeutical unit being connected to each of the utility units, each of the utility units having transducing means for converting at least one of input energies in the selected form into an output energy adapted for the therapeutical instrument unit corresponding to the utility unit, the therapeutical instrument unit being actuated by the output of the transducing means, in which said connecting means is provided with an electric micro-motor which is driven by an electric energy supplied from said energy supply unit, and said transducing means comprises a dynamo-generator which is axially driven by said electric micro-motor to generate electric energy, and regulating means for electrically regulating the electric output energy of said dynamo-generator.

9. A dental therapeutical apparatus comprising a common energy supply unit for supplying a plurality of energies of different forms, a plurality of utility units selectively connectable to the energy supply unit, connecting means for selectively connecting the energy supply unit and each of the utility units, which supplies the energy in the form selected out of the plurality of energies to each of the utility units, and a therapeutical instrument unit adapted for therapeutical purposes different from each other, the therapeutical unit being connected to each of the utility units, each of the utility units having transducing means for converting at least one of input energies in the selected form into an output energy adapted for the therapeutical instrument unit corresponding to the utility unit, the therapeutical instrument unit being actuated by the output of the transducing means, in which at least one of said transducing means in said utility units comprises a dynamo-generator which is axially driven by an impeller to generate electric energy, the impeller being disposed in said utility unit and rotatable by a pressurized air supplied from said energy supply unit into said utility unit.

* * * * *